(12) United States Patent
Larson

(10) Patent No.: US 7,190,639 B2
(45) Date of Patent: Mar. 13, 2007

(54) METHOD AND APPARATUS FOR MEASURING FLUID VISCOSITY USING ELECTRIC CONDUCTANCE

(76) Inventor: David C. Larson, 303 N. Eastwood Ave., Mount Prospect, IL (US) 60056

( * ) Notice: Subject to any disclaimer, the term of this patent is extended or adjusted under 35 U.S.C. 154(b) by 366 days.

(21) Appl. No.: 10/756,003

(22) Filed: Jan. 13, 2004

(65) Prior Publication Data

US 2004/0141183 A1 Jul. 22, 2004

Related U.S. Application Data

(60) Provisional application No. 60/439,957, filed on Jan. 14, 2003.

(51) Int. Cl.
*G01N 11/06* (2006.01)
(52) U.S. Cl. .................... 368/113; 73/54.13
(58) Field of Classification Search ............ 368/107, 368/113, 121; 73/54.01–54.07, 54.11, 54.13; 234/306, 458; 324/306, 306 F
See application file for complete search history.

(56) References Cited

U.S. PATENT DOCUMENTS

| | | |
|---|---|---|
| 3,187,563 A | 6/1965 | Tobias |
| 3,680,362 A * | 8/1972 | Geerdes et al. ............ 73/54.13 |
| 4,662,030 A | 5/1987 | Cooper et al. |

OTHER PUBLICATIONS

American Society for Testing Materials, "Standard Test Method for Viscosity by Dip-Type Viscosity Cups," ASTM Designation D 4212-99, 1999.

Graymills Corporation, Graymills New Expanded Catalog, Sep. 1999.

* cited by examiner

*Primary Examiner*—Vit Miska
*Assistant Examiner*—Sean Kayes
(74) *Attorney, Agent, or Firm*—McAndrews, Held & Malloy, Ltd.

(57) ABSTRACT

An apparatus uses electrical conductance to determine the start and stop times for viscosity measurements using efflux cups. An efflux cup and two probes are immersed and removed from the fluid. An electric current is applied between each probe and the efflux cup. A timer measures the elapsed time between a decrease in the electric current measured between a first probe and the efflux cup and a decrease in the electric current measured between a second probe and the efflux cup.

7 Claims, 3 Drawing Sheets

1

METHOD AND APPARATUS FOR MEASURING FLUID VISCOSITY USING ELECTRIC CONDUCTANCE

CROSS-REFERENCE TO RELATED APPLICATIONS

The present application relates to, and claims priority benefits from U.S. Provisional Patent Application Ser. No. 60/439,957 filed on Jan. 14, 2003, entitled "Method and Apparatus for Measuring Fluid Viscosity Using Electric Conductance". The '957 provisional application is incorporated by reference herein in its entirety.

FIELD OF THE INVENTION

The present invention relates to the measurement of fluid viscosity using electric conductance, and more particularly to a method and apparatus for measuring fluid viscosity by reference to the electric conductance of the fluid.

BACKGROUND OF THE INVENTION

Viscosity is the measurement of a fluid's resistance to flow. Viscosity is an important property that is commonly measured and/or controlled with respect to fluids employed in the printing and coating industries. One current method to measure viscosity is to measure the time it takes for a volume of fluid to flow out of a cup with a specified diameter hole in the bottom of the cup. This type of cup is generically referred to as an efflux cup. The time measurement, in seconds, is converted into units called centistokes (cSt).

Centistokes are defined by multiplying the viscosity (in centipoise) by the specific gravity of a fluid. Thus, viscosity (in centipoise) can be calculated by dividing centistokes by the specific gravity of the fluid. Although indirect, this calculation provides a quick and inexpensive way to measure the complex property of fluid viscosity.

Efflux cups are available in various shapes and sizes, and are widely available. Common types of efflux cups include Zahn, Shell and Ford cups. The most common type of efflux cup used commercially today is the ZAHN cup. ZAHN cups are commercially available in different size ranges, denoted 1–5, and are differentiated by the diameter of the bottom drain or orifice.

Because the ZAHN cup is so common and widely used, the term "Zahn" has become an eponym. In this regard, the experimental units of time reported for drainage of fluids from a ZAHN cup are referred to as Zahn-seconds. Today it is common to report viscosity simply as X number of Y Zahn-seconds (for example, 15.5 #2 Zahn-seconds), where X is the drainage time measured in seconds, and Y is the number of the ZAHN cup. Similarly, one can state units as Shell seconds when using a Shell cup or Ford seconds when using a Ford cup, for example. Rarely do users convert these times into centistokes or centipoise.

The drainage times of fluids draining from efflux cups can be standardized by measuring the time between a starting time and a stop time. For example, an efflux cup is placed into and removed from a fluid. The starting time occurs as soon as the top rim of the efflux cup breaks the surface of the fluid upon removal. The fluid then proceeds to drain from the efflux cup through the orifice in the bottom of the cup. The stop time is defined as the instant the stream of fluid breaks between 1 and 2 inches below the efflux cup. That is, the stop time occurs when a continuous stream of fluid draining from the hole in the efflux cup becomes non-continuous between 1 and 2 inches below the efflux cup.

Currently, the drainage times are measured by manually starting and stopping a stopwatch after visual interpretation of the start and stop times. Problems with this approach are obvious: operator reaction time and varying interpretations of start and stop times. These problems lessen the accuracy and precision of the viscosity measurement.

Proposed solutions to these accuracy and precision problems include using floats, levers and even optical emitter/detector pairs to determine the start and stop times. However, many times the fluid being measured can remain on the float, lever or optical emitter/detector pair and interfere with the measurement of either the stop or start time. That is, the fluid can coat the device and interfere with the device's measurements. For example, ink that remains on an optical detector can cause inaccurate or false measurements of the start or stop times.

One solution that has yet to be employed is the use of electric current and the ability of the fluid to conduct the electric current to more accurately and precisely measure the drainage start and stop times. That is, a new solution is to utilize the electric conductance of a fluid to measure the start and stop times.

A device, capable of being added to any conventional viscosity measuring cup, and which could accurately determine start and stop times would virtually eliminate human error associated with conventional viscosity measurements. This, along with simplicity and speed, is one of the main goals in automating viscosity-testing instrumentation.

SUMMARY OF THE INVENTION

The above and other objects are achieved by a method and apparatus that determines an elapsed amount of time between a start and stop time in viscosity measurements using efflux cups, electric current and an electrically conductive fluid. An efflux cup, a first probe and a second probe are immersed into an electrically conductive fluid. An electric current is applied between the first probe and the efflux cup and between the second probe and the efflux cup. The electric current passes from the probes to the efflux cup across an electrically conductive path created by the fluid. When the probes and the efflux cup are removed from the fluid, the fluid in the efflux cup begins to drain through the orifice. As the electrically conductive path created by the fluid between the first probe and the efflux cup is interrupted, a signal is sent to a timer. The signal commands the timer to actuate and begin measuring an amount of time elapsed. The timer continues to measure the elapsed amount of time until the fluid path and thus the electric current between the second probe and the efflux cup decreases or is interrupted. As the electric current between the second probe and the efflux cup is decreased or interrupted, a signal is sent to the timer, commanding the timer to deactivate and stop measuring the elapsed amount of time. In this way, the current apparatus and method are able to more accurately and precisely determine the start and stop times of drainage seconds of an efflux cup.

In another embodiment, the first and second probes are removably attached from the efflux cup. In this way, the probes can be easily removed or attached to any existing efflux cup.

In another embodiment, the timer does not begin measuring the elapsed amount of time until the amount of electric current measured between the first probe and the efflux cup decreases below a threshold amount.

In another embodiment, the timer does not stop measuring the elapsed amount of time until the amount electric current measured between the second probe and the efflux cup decreases below a threshold amount.

In another embodiment, the timer does not begin measuring the elapsed amount of time until the amount of electric current measured between the first probe and the efflux cup decreases below a threshold amount for a threshold amount of time.

In another embodiment, the timer does not stop measuring the elapsed amount of time until the amount of electric current measured between the second probe and the efflux cup decreases below a threshold amount for a threshold amount of time.

DETAILED DESCRIPTION OF PREFERRED EMBODIMENT(S)

Figure 1:
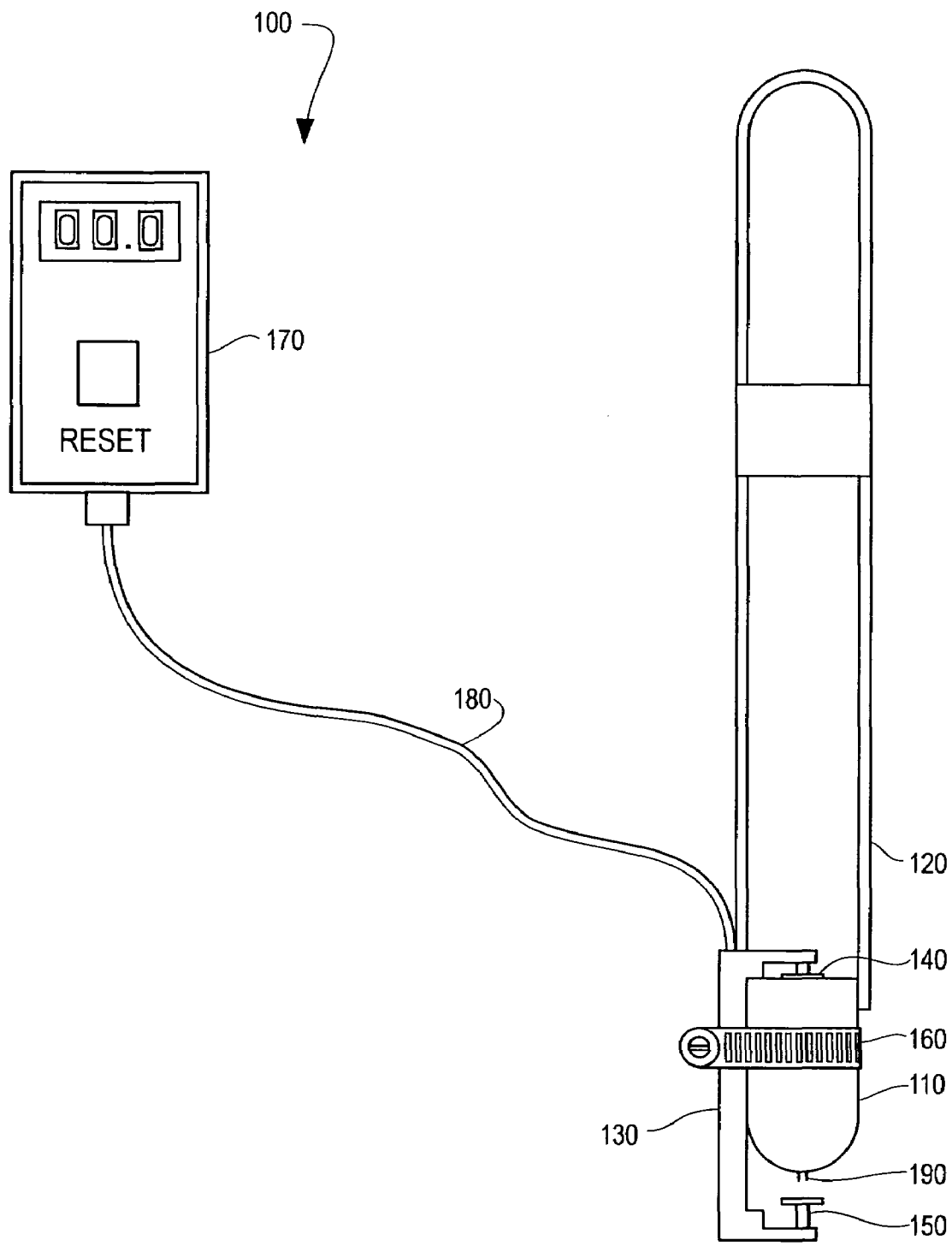
FIG. 1 is a plan view of the viscosity measurement apparatus.

FIG. 1 is a plan view a preferred embodiment of viscosity measurement apparatus 100. Viscosity measurement apparatus 100 includes an efflux cup 110, an efflux cup handle 120, a bracket 130, a first probe 140, a second probe 150, a clamp 160, an electronic readout 170 and a wire 180. The efflux cup 110 is connected to the efflux cup handle 120. Efflux cup 110 includes an orifice 190 in the bottom of the efflux cup 110. Orifice 190 can be a standard diameter. For example, orifice 190 can be a standard diameter for a ZAHN cup commonly the efflux cup 110, efflux cup handle 120 and orifice 190 can be a standard ZAHN cup device commonly used in the measurement of viscosity.

Bracket 130 is connected to efflux cup 110 by clamp 160. First probe 140 and second probe 150 are connected to bracket 130. First probe 140 can extend from bracket 130 towards the lip of efflux cup 110. First probe 140 preferably extends to the lip of efflux cup 110. That is, first probe 140 can extend perpendicular to a plane defined by the lip of efflux cup 110. First probe 140 can then preferably extend to the plane defined by efflux cup 110 lip. In this way, when efflux cup 110 is filled with a fluid, first probe 140 preferably contacts the fluid.

Second probe 150 can be preferably located underneath the orifice 190. Both first probe 140 and second probe 150 are connected electronically to wire 180. Wire 180 electronically connects first probe 140, second probe 150 and efflux cup 110 to electronic readout 170.

Figure 2:
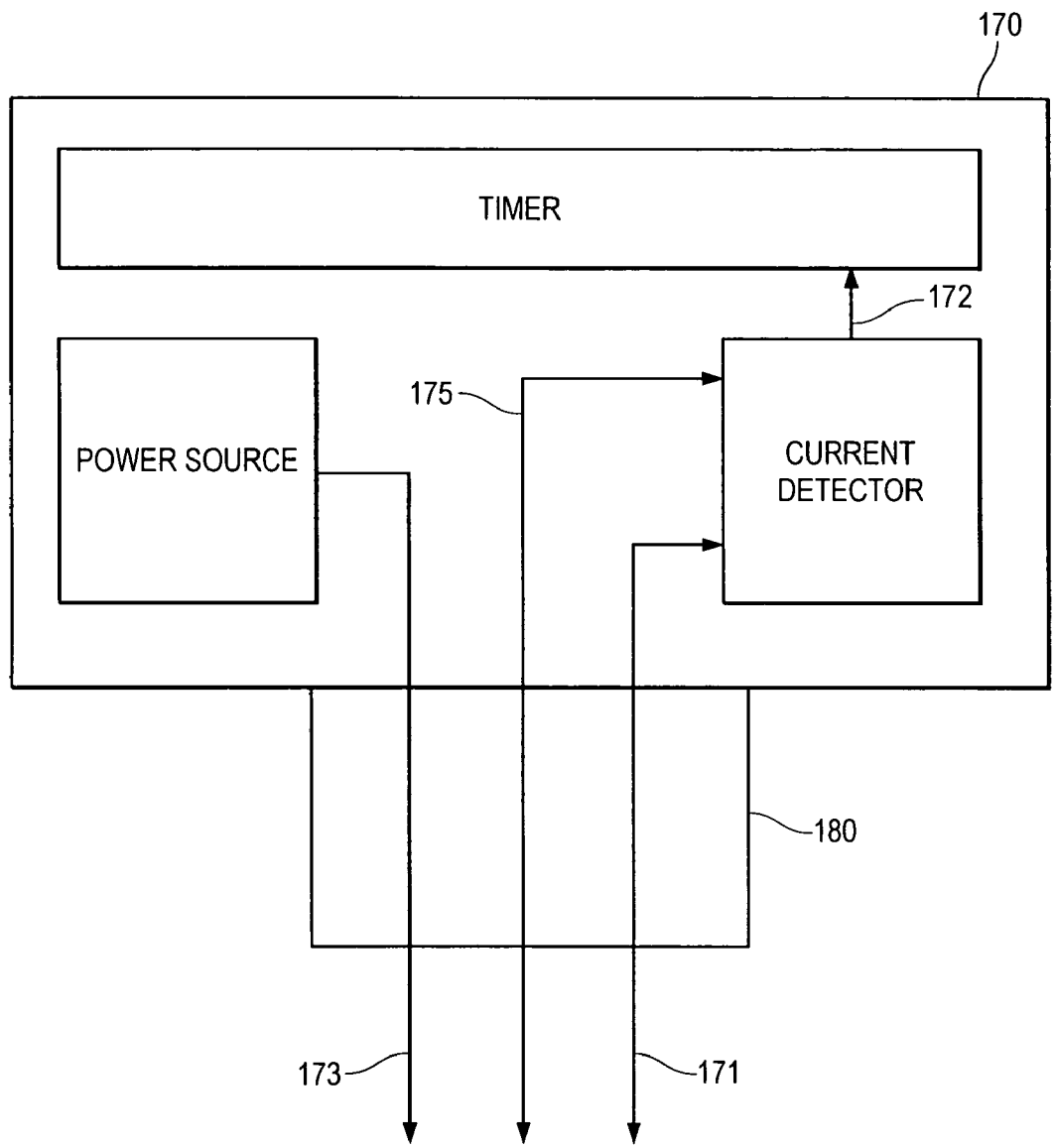
FIG. 2 depicts the electronic readout of FIG. 1 according to a preferred embodiment of the present viscosity measurement apparatus.

FIG. 2 depicts electronic readout 170 of FIG. 1 according to a preferred embodiment of the present viscosity measurement device. Electronic readout 170 includes a timer 174, a power source 176 and an electric current detector 178. Electronic readout 170 is connected to wire 180. Timer 174 is electronically connected to electric current detector 178. Wire 180 includes first probe 140 current signal 171, second probe 150 current signal 175 and alternating current 173. Electric current detector 178 is electronically connected to first probe 140 by first probe 140 current signal 171. Electric current detector 178 is electronically connected to second probe 150 by second probe 150 current signal 175. First probe 140 current signal 171 can be a measured amount of electric current passing between first probe 140 and efflux cup 110, for example. Second probe 150 current signal 175 can be a measured amount of electric current passing between second probe 150 and efflux cup 110, for example.

Electric current detector 178 can send a timing communication signal 172 to timer 174. Power source 176 is connected to first probe 140 and second probe 150 by an alternating current 173.

In operation, electronic readout 170 preferably provides alternating current 173 from power source 176 to first probe 140 and second probe 150 through wire 180. When the operator holds viscosity measurement apparatus 100 by handle 120 and submerges first probe 140, second probe 150 and efflux cup 110 in an electrically conductive fluid, efflux cup 110 preferably fills with the fluid. The electrically conductive fluid can allow alternating current 173 sent from power source 176 through wire 180 to first probe 140 to pass from first probe 140 to efflux cup 110. In addition, the fluid can allow alternating current 173 send from power source 176 through wire 180 to second probe 150 to pass from second probe 150 to efflux cup 110. In this way, for example, when efflux cup 110, first probe 140 and second probe 150 are submerged in the fluid, alternating current 173 can flow from first probe 140 to efflux cup 110 and from second probe 150 to efflux cup 110.

Once efflux cup 110 and first probe 140 are submerged in the electrically conductive fluid, wire 180 can carry first probe 140 current signal 171 from first probe 140 to electric current detector 178 of electronic readout 170. In addition, wire 180 can carry second probe 150 current signal 175 from second probe 150 to electric current detector 178. That is, when the electrically conductive fluid creates a conductive path between first probe 140 and efflux cup 110, first probe 140 current signal 171 can be carried from first probe 140 to electric current detector 178. First probe 140 current signal 171 can indicate if electric current is flowing between first probe 140 and efflux cup 110, for example. Electric current detector 178 can then receive first probe 140 current signal 171 and therefore determine that electric current is passing between first probe 140 and efflux cup 110, for example.

Similarly, when the fluid creates a conductive path between second probe 150 and efflux cup 110, second probe 150 current signal 175 can be carried from second probe 150 to electric current detector 178. That is, when the electrically conductive fluid creates a conductive path between second probe 150 and efflux cup 110, second probe 150 current signal 175 can be carried from second probe 150 to electric current detector 178. Second probe 150 current signal 175 can indicate if electric current is flowing between second probe 150 and efflux cup 110, for example. Electric current detector 178 can then receive second probe 150 current signal 175 and therefore determine that electric current is passing between second probe 150 and efflux cup 110, for example.

If electric current detector 178 receives both first probe 140 current signal 171 and second probe 150 current signal 175, for example, electric current detector 178 can send a "RESET" timing communication signal 172 to timer 174. That is, electric current detector 178 can send a timing communication signal 172 to timer 174 causing timer 174 to reset any stored time value to zero. For example, if timer 174 has a stored time value of 14.8 seconds, timing communication signal 172 can cause timer 174 to set the time value to zero. Timer 174 can be, for example, analogous to a stopwatch. In this way, when timer 174 is reset, the analogous stopwatch can be reset to zero.

After timer 174 is reset, for example, the operator can then remove viscosity measurement apparatus 100 from the fluid. Preferably, top probe 140, bottom probe 150 and efflux cup 110 are completely removed from the fluid. When the lip of efflux cup 110 breaks the surface of the fluid, first probe 140 can be preferably removed from fluid. As first probe 140 is removed from the fluid, an electrically conductive path between first probe 140 and efflux cup 110 can be interrupted. That is, as the electrically conductive fluid may no longer exist between first probe 140 and efflux cup 110, for example, a decreased or terminated electrically conductive path can decrease or prevent electric current from passing between first probe 140 and efflux cup 110. As decreased or no electric current passes between first probe 140 and efflux cup 110, first probe 140 current signal 171 may decrease or terminate, for example. That is, first probe 140 current signal 171 can have little or no measurable value when the electric current between first probe 140 and efflux cup 110 sufficiently decreases or altogether terminates, for example. Therefore, electric current detector 178 can determine that the current between first probe 140 and efflux cup 110 no longer exists, for example.

When electric current detector 178 determines that first probe 140 current signal 171 no longer exists (that is, that the electrically conductive path between first probe 140 and efflux cup 110 has been interrupted), electric current detector 178 can send a "START" timing communication signal 172 to timer 174, for example. That is, electric current detector 178 can send a timing communication signal 172 to timer 174 directing timer 174 to begin tracking time. Returning to the analogy of timer 174 to a stopwatch, the stopwatch begins tracking the amount of time elapsed since "START" timing communication signal 172 is received, for example.

Timer 174 can display the current elapsed time in a display window of electronic readout 170. Timer 174 preferably advances time in increments of 0.1 seconds. The current elapsed time can be updated on a regular or periodic basis.

As the fluid drains through orifice 190 in the bottom of efflux cup 110, timer 174 continues to measure the amount of time elapsed. The fluid can create a continuous stream extending from orifice 190 to second probe 150. The continuous stream of fluid creates an electrically conductive path between efflux cup 110 and second probe 150. In this way, power source 176 continues to supply current 173 to second probe 150 and electric current continues to flow between second probe 150 and efflux cup 110. Therefore, second probe 150 current signal 175 can continue to exist as long as electric current exists between second probe 150 and efflux cup 110, for example.

At some later point in time, the continuous stream of fluid extending from orifice 190 of efflux cup 110 can begin to become non-continuous. That is, the stream of fluid draining from efflux cup 110 can become interrupted. The amount of time before the continuous stream of fluid becomes interrupted can be dependent upon the viscosity of the fluid, as discussed above. When the stream of fluid becomes interrupted, the electric current between second probe 150 and efflux cup 110 can become interrupted. Therefore, second probe 150 current signal 175 may become interrupted. That is, if the electrically conductive path between second probe 150 and efflux cup 110 becomes interrupted, then the current passing between second probe 150 and efflux cup 110 may become interrupted, for example. If electric current detector 178 determines that second probe 150 current signal 175 has become interrupted, electric current detector 178 sends a "STOP" timing communication signal 172 to timer 174, for example. When timer 174 receives "STOP" timing communication signal 172 from electric current detector 178, timer 174 can stop tracking the amount of time elapsed since first probe 140 current signal 171 terminated, for example. That is, timer 174 can stop advancing the time displayed on electronic readout 170.

When timer 174 stops tracking the time elapsed since first probe 140 current signal 171 terminated, the operator of viscosity measurement apparatus 100 can obtain the amount of time elapsed from timer 174 display. That is, the operator can obtain the amount of elapsed time from timer 174 on electronic readout 170 once timer 174 stops tracking the elapsed time.

In another embodiment of present apparatus 100, bracket 130 can be attached to efflux cup handle 120 instead of efflux cup 110. In this way, bracket 130 can be attached to handle 120 above efflux cup 110.

In another embodiment of present apparatus 100, bracket 130 can be removably attached to either efflux cup 110 or handle 120. That is, bracket 130 can be easily removable from either handle 120 or efflux cup 110. In this way, the portion of viscosity measurement apparatus 100 comprising bracket 130, first probe 140 and second probe 150 can be easily replaceable by simply detaching bracket 130 from either efflux cup 110 or handle 120.

In another embodiment of the present apparatus, either first probe 140 or second probe 150, or both first probe 140 and second probe 150 can be removably attached to efflux cup 110 or handle 120. That is, either first probe 140 or second probe 150 can be easily detached or re-attached to either efflux cup 110 or handle 120.

In another embodiment of present apparatus 100, the position of either first probe 140 or second probe 150 can be adjusted. That is, first probe 140 or second probe 150 can be adjusted in either a vertical or horizontal direction. In this way, if first probe 140 does not extend to the plane defined by the lip of efflux cup 110, then first probe 140 can be adjusted downwards so that probe 140 does extend to at least the top of efflux cup 110, for example. Similarly, second probe 150 can be adjusted vertically towards or away from efflux cup 110. For example, the operator may desire to adjust the point below efflux cup 110 at which the continuous stream of fluid draining from efflux cup 110 can be measured. In addition, the operator may require that second probe 150 be adjusted in a horizontal direction (that is, a direction perpendicular to the long axis of efflux cup 110) so that second probe 150 is located below orifice 190, for example.

In another embodiment of present apparatus 100, once efflux cup 110, first probe 140 and second probe 150 are submerged in the electrically conductive fluid, electric current detector 178 can then receive first probe 140 current signal 171 and second probe 150 current signal 175. Electric current detector 178 can then compare either or both first probe 140 current signal 171 and/or second probe 150 current signal 175 to a threshold electric current. If either or both first probe 140 current signal 171 and/or second probe 150 current signal 175 are greater than the threshold electric current, for example, electric current detector 178 sends a "RESET" timing communication signal 172 to timer 174. That is, electric current detector 178 can send signal to timer 174 causing timer 174 to reset any stored time value to zero.

Similarly, in another embodiment of present apparatus 100, as first probe 140 is removed from the fluid and the electrically conductive path between first probe 140 and efflux cup 110 may be interrupted, first probe 140 current signal 171 may decrease or terminate, for example. Electric current detector 178 can then compare first probe 140 current signal 171 to a threshold electric current. If, for example, first probe 140 current signal 171 is smaller than the threshold electric current, then electric current detector 178 can send a "START" timing communication signal 172 to timer 174, for example. That is, electric current detector 178 can send a timing communication signal 172 to timer 174 directing timer 174 to begin tracking time.

Similarly, in another embodiment of present apparatus 100, as the stream of fluid draining from orifice 190 of efflux cup 110 may become interrupted, electric current detector 178 can compare second probe 150 current signal 175 to a threshold electric current. If second probe 150 current signal 175 is smaller than the threshold electric current, for example, electric current detector 178 can then send a "STOP" timing communication signal 172 to timer 174, for example. When timer 174 receives "STOP" timing communication signal 172 from electric current detector 178, timer 174 can stop tracking the amount of time elapsed since first probe 140 current signal 171 terminated, for example. That is, timer 174 can stop advancing the time displayed on electronic readout 170.

In another embodiment of present apparatus 100, once efflux cup 110, first probe 140 and second probe 150 are submerged in the electrically conductive fluid, electric current detector 178 can then receive first probe 140 current signal 171 and second probe 150 current signal 175. Electric current detector 178 can then determine if first probe 140 current signal 171 and second probe 150 current signal 175 have a threshold value of electric current for a threshold amount of time, for example. That is, electric current detector 178 can determine if first probe 140 current signal 171 and second probe 150 current signal 175 both have a measurable value greater than a threshold electric current, for example, for a threshold amount of time. If both first probe 140 current signal 171 and second probe 150 current signal 175 do have a threshold value of electric current, for example, for a threshold amount of time, then electric current detector 178 can send a "RESET" timing communication signal 172 to timer 174. That is, electric current detector 178 can send signal to timer 174 causing timer 174 to reset any stored time value to zero. For example, if first probe 140 electric signal 171 and second probe 150 electric signal 175 both have a threshold value of electric current for 0.5 seconds, and the threshold interruption period is 0.3 seconds, then electric current detector 178 can send a "RESET" timing communication signal 172 to timer 174.

Similarly, in another embodiment of present apparatus 100, as first probe 140 is removed from the fluid and the electrically conductive path between first probe 140 and efflux cup 110 may be interrupted, first probe 140 current signal 171 may decrease or terminate, for example. Electric current detector 178 can then determine if first probe 140 current signal 171 is smaller than a threshold electric current, for example, for a threshold amount of time. If first probe 140 current signal 171 is smaller than a threshold electric current for a threshold amount of time, for example, then electric current detector 178 can send a "START" timing communication signal 172 to timer 174, for example. That is, electric current detector 178 can send a timing communication signal 172 to timer 174 directing timer 174 to begin tracking time. For example, if first probe 140 current signal 171 is smaller than a threshold electric current for 0.5 seconds, and the threshold amount of time is 0.3 seconds, then electric current detector 178 can send a "START" timing communication signal 172 to timer 174, for example.

Similarly, in another embodiment of present apparatus 100, as the stream of fluid draining from orifice 190 of efflux cup 110 may become interrupted, second probe 150 current signal 175 may decrease or terminate, for example. Electric current detector 178 can then determine if second probe 150 current signal 175 is smaller than a threshold electric current, for example, for a threshold amount of time. If second probe 150 current signal 175 is smaller than the threshold electric current for a threshold amount of time, for example, then electric current detector 178 can send a "STOP" timing communication signal 172 to timer 174, for example. When timer 174 receives "STOP" timing communication signal 172 from electric current detector 178, timer 174 can stop tracking the amount of time elapsed since first probe 140 current signal 171 terminated, for example. That is, timer 174 can stop advancing the time displayed on electronic readout 170. For example, if second probe 150 current signal 175 is smaller than a threshold electric current for 0.5 seconds, and the threshold amount of time is 0.3 seconds, then electric current detector 178 can send a "STOP" timing communication signal 172 to timer 174.

Figure 3:
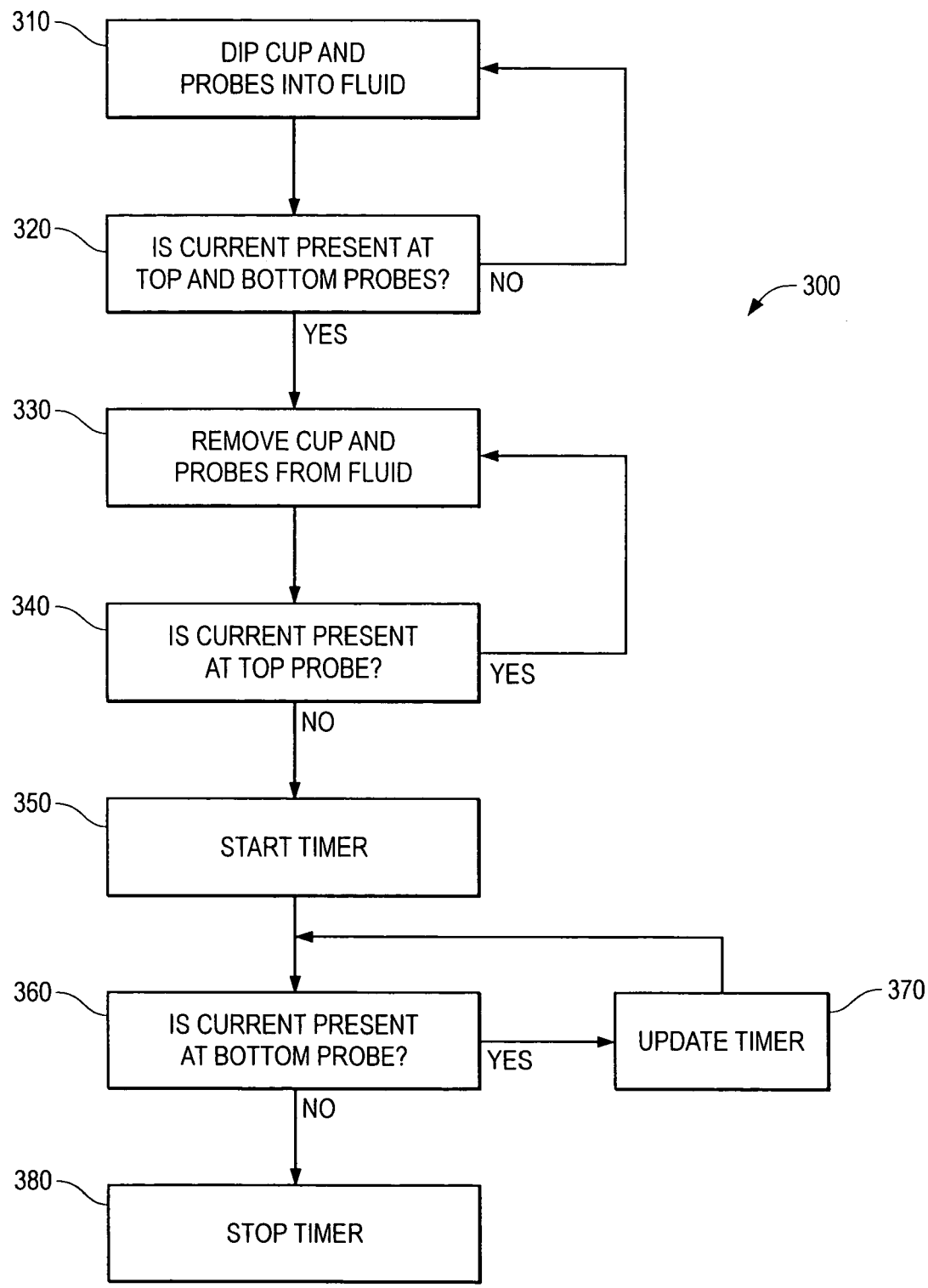
FIG. 3 depicts a flowchart of a method for determining the start and stop times in viscosity measurements using efflux cups.

FIG. 3 depicts a flowchart for a method 300 for determining the start and stop times in viscosity measurements using efflux cups. First, at step 310, an efflux cup with an electric probe at the top of the cup (the top probe) and an electric probe below the orifice of the cup (the bottom probe) can be placed into an electrically conductive fluid. The cup and probes can be completely immersed in the fluid. The two probes can be supplied with electric current, preferably alternating current.

Next, at step 320, the existence of electric current between the top probe and the efflux cup and between the bottom probe and the efflux cup can be determined. If no electric current is found between the top probe and the efflux cup or between the bottom probe and the efflux cup, then method 300 proceeds to step 310 where the efflux cup, the top probe and the bottom probe can be again immersed in the electrically conductive fluid. That is, if no electric current is found between the efflux cup and either probe, then the efflux cup and the two probes have not been sufficiently submersed in the fluid. Therefore, method 300 proceeds to re-introduce the efflux cup and probes into the fluid. However, if electric current is found between the top probe and the efflux cup and between the bottom probe and efflux cup, then method 300 proceeds to step 330.

At step 330, efflux cup, the top probe and the bottom probe can be completely removed from the fluid. The fluid can then drain from the bottom orifice of the efflux cup onto the bottom probe. Next, at step 340, the existence of electric current between the top probe and the efflux cup can be determined. If electric current is found between the top probe and the efflux cup, then method 300 proceeds to step 330 where the efflux cup, the top probe and the bottom probe can be removed from the fluid. That is, if electric current is detected between the top probe and the efflux cup, then the efflux cup and probes have not been sufficiently removed from the fluid. Therefore, the efflux cup and probes can be further removed from the fluid.

Conversely, if no electric current is found between the top probe and the efflux cup, then method 300 proceeds to step 350. That is, if the previous electric current between the top probe and efflux cup is terminated, for example, method 300 proceeds to step 350.

At step 350, a timer can be started. That is, a time-keeping device such as an electric timer is started, for example. The timer can measure an elapsed time. The elapsed time can be the amount of time elapsed since the electric current between the top probe and the efflux cup was terminated.

Next, at step 360, the existence of electric current between the bottom probe and the efflux cup can be determined. If electric current is found between the bottom probe and the efflux cup, then the method proceeds to step 370. That is, if the electrically conductive fluid draining from the efflux cup onto the bottom probe has a continuous flow such that electric current can flow from the bottom probe to the efflux cup, then electric current can be detected, for example. However, if no electric current is found between the bottom probe and the efflux cup, then the method proceeds to step 380. That is, if the flow of the electrically conductive fluid draining from the efflux cup becomes interrupted, then electric current flowing between the bottom probe and the efflux cup can become interrupted, for example.

At step 370, the timer can be updated. That is, the timer increases by a given incremental step. For example, the timer can increase the elapsed time by 0.1 seconds. Method 300 then proceeds to step 360.

At step 380, the timer can be stopped. That is, when an interruption in the electric current between the bottom probe and the efflux cup is found, the timer can be stopped from measuring the elapsed time any further. The elapsed time measured by the timer can therefore be equivalent to the time elapsed between the start and stop times in viscosity measurements using efflux cups. In this way, the operator can obtain the number of Zahn-seconds for a given fluid, for example.

In another embodiment of present method 300, at step 320 the electric current between the top probe and the efflux cup and between the bottom probe and the efflux cup can be compared to a threshold. If the current between the top probe and the efflux cup or between the bottom probe and the efflux cup is below a given threshold of electric current, then method 300 proceeds to step 310 where the efflux cup, the top probe and the bottom probe can be again immersed in the electrically conductive fluid. That is, if the electric current between the efflux cup and either probe is smaller than a threshold electric current, then the efflux cup and the two probes have not been sufficiently submersed in the fluid. Therefore method 300 proceeds to re-introduce the efflux cup and probes into the fluid. However, if electric current above a threshold electric current is found between the top probe and the efflux cup and between the bottom probe and the efflux cup, then method 300 proceeds to step 330.

Similarly, in another embodiment of method 300, at step 340 the electric current between the top probe and the efflux cup can be compared to a threshold. For example, if the current between the top probe and the efflux cup is greater than a given threshold of electric current, then method 300 proceeds to step 330 where the efflux cup, the top probe and the bottom probe can be removed from the fluid. That is, if electric current greater than a threshold electric current is detected between the top probe and the efflux cup, then the efflux cup and probes may have not been sufficiently removed from the fluid. Therefore, the efflux cup and probes can be further removed from the fluid.

Conversely, if an electric current found between the top probe and the efflux cup is below a threshold electric current, then method 300 can proceed to step 350. That is, if the previous electric current between the top probe and efflux cup is below a threshold electric current, method 300 can proceed to step 350.

Similarly, in another embodiment of present method 300, at step 360 the electric current between the bottom probe and the efflux cup can be compared to a threshold electric current. If the electric current between the bottom probe and the efflux cup is greater than a threshold electric current, then method 300 can proceed to step 370. Conversely, if the electric current between the bottom probe and the efflux cup is less than a threshold electric current, then the method can proceed to step 380.

In another embodiment of present method 300, at step 320 the existence of any interruptions in electric current flowing between the top probe and the efflux cup and between the bottom probe and the efflux cup can be compared to a threshold interruption period. That is, an amount of time that electric current flowing between the top probe and the efflux cup or between the bottom probe and the efflux cup is interrupted can be compared to a threshold interruption time. If the amount of time that the electric current is interrupted is less than the threshold interruption period, then the method 300 can proceed to step 330. Conversely, if the amount of time that the electric current is interrupted is greater than or equal to the threshold interruption period, then method 300 can proceed to step 310. For example, if the electric current between either the top probe or the bottom probe and the efflux cup is interrupted for 0.1 seconds, and the threshold interruption period is 0.3 seconds, then the electric current has not been sufficiently interrupted and method 300 can proceed to step 320. This can occur, for example, when any interruption in electric current between either probe and the efflux cup is sufficiently small not to warrant the re-introduction of the efflux cup and probes back into the liquid.

Alternatively, for example, if the electric current between either the top or bottom probe and the efflux cup is interrupted for 0.5 seconds, and the threshold interruption period is 0.3 seconds, then the electric current has been sufficiently interrupted and method 300 can proceed to step 310. This can occur, for example, when the efflux cup and probes have not been sufficiently submersed in the electrically conductive fluid and are re-introduced into the fluid.

Similarly, in another embodiment of present method 300, at step 340 the existence of any interruptions in electric current flowing between the top probe and the efflux cup can be compared to a threshold interruption period. That is, an amount of time that electric current flowing between the top probe and the efflux cup is interrupted can be compared to a threshold interruption time. If the amount of time that the electric current is interrupted is less than the threshold interruption period, then method 300 can proceed to step 330. Conversely, if the amount of time that the electric current is interrupted is greater than or equal to the threshold interruption period, then method 300 can proceed to step 350. For example, if the electric current between the top probe and the efflux cup is interrupted for 0.1 seconds, and the threshold interruption period is 0.3 seconds, then the electric current has not been sufficiently interrupted and method 300 can proceed to step 330. This can occur, for example, when the probes and the efflux cup have not been sufficiently removed from the electrically conductive fluid. Therefore, the probes and efflux cup are further removed from the fluid, for example.

Alternatively, for example, if the electric current between the top probe and the efflux cup is interrupted for 0.5 seconds, and the threshold interruption period is 0.3 seconds, then the electric current has been sufficiently interrupted and method 300 can proceed to step 350. This can occur, for example, when the probes and the efflux cup have been sufficiently removed from the electrically conductive fluid, for example.

In another embodiment of present method 300, at step 360 the existence of any interruptions in electric current flowing between the bottom probe and the efflux cup can be compared to a threshold interruption period. That is, an amount of time that electric current flowing between the bottom probe and the efflux cup is interrupted can be compared to a threshold interruption time. If the amount of time that the electric current is interrupted is less than the threshold interruption period, then method 300 can proceed to step 370. Conversely, if the amount of time that the electric current is interrupted is greater than or equal to the threshold interruption period, then method 300 can proceed to step 380. For example, if the electric current between the bottom probe and the efflux cup is interrupted for 0.1 seconds, and the threshold interruption period is 0.3 seconds, then the electric current has not been sufficiently interrupted and method 300 can proceed to step 370. This can occur, for example, when the continuous draining of the electrically conductive fluid is interrupted only very briefly.

Alternatively, for example, if the electric current between the bottom probe and the efflux cup is interrupted for 0.5 seconds, and the threshold interruption period is 0.3 seconds, then the electric current has been sufficiently interrupted and method 300 can proceed to step 380. This can occur, for example, when the continuous draining of the electrically conductive fluid has been sufficiently interrupted.

While particular steps, elements, embodiments and applications of the present invention have been shown and described, it will be understood, of course, that the invention is not limited thereto since modifications can be made by persons skilled in the art, particularly in light of the foregoing teachings. It is therefore contemplated by the appended claims to cover such modifications as incorporate those steps or elements that come within the scope of the invention.

What is claimed is:

1. A method for determining the start and stop times in viscosity measurements using an efflux cup, the method comprising:

(a) immersing an efflux cup, a first probe and a second probe in an electrically conductive fluid;
(b) applying an applied electronic current between said first probe and said efflux cup and between said second probe and said efflux cup;
(c) removing said efflux cup, said first probe and said second probe from said fluid,
wherein said fluid drains through an orifice in said efflux cup onto said second probe;
(d) starting a timer when a first measured electric current between said first probe and said efflux cup decreases; and
(e) stopping said timer when a second measured electric current between said second probe and said efflux cup decreases.

2. The method of claim 1, wherein said starting step occurs when said first measured electric current decreases below a threshold amount of electric current.

3. The method of claim 2, wherein said starting step occurs when said first measured electric current decreases below said threshold amount of electric current for a threshold amount of time.

4. The method of claim 1, wherein said stopping step occurs when said second measured electric current decreases below a threshold amount of electric current.

5. The method of claim 4, wherein said stopping step occurs when said second measured electric current decreases below said threshold amount of electric current for a threshold amount of time.

6. The method of claim 1, wherein said applying step includes applying a first electric current between said first probe and said efflux cup across a first conductive path created by said fluid and applying a second electric current between said second probe and said efflux cup across a second conductive path created by said fluid.

7. The method of claim 1, wherein said applying step includes applying a first electric current between said first probe and said efflux cup and a second electric current between said second probe and said efflux cup, wherein said first electric current differs from said second electric current.

* * * * *